(12) United States Patent
Nakamura et al.

(10) Patent No.: US 6,790,409 B1
(45) Date of Patent: Sep. 14, 2004

(54) METHOD OF DISINFECTING CONTACT LENS AND DISINFECTING LIQUID FOR THE METHOD

(75) Inventors: Chikako Nakamura, Nagoya (JP); Kazuhiko Nakada, Nisshin (JP); Tatsuya Hayashi, Nagoya (JP); Kotaro Sakanishi, Komaki (JP)

(73) Assignee: Menicon Co., Ltd., Nagoya (JP)

( * ) Notice: Subject to any disclaimer, the term of this patent is extended or adjusted under 35 U.S.C. 154(b) by 527 days.

(21) Appl. No.: 09/698,596

(22) Filed: Oct. 27, 2000

(30) Foreign Application Priority Data

Nov. 1, 1999 (JP) .............................. 11-311487
Sep. 26, 2000 (JP) ........................ 2000-292664

(51) Int. Cl.[7] .......................... A61L 12/06; A61L 12/12
(52) U.S. Cl. .............................. 422/22; 422/23; 422/24; 422/28; 424/600; 424/616; 510/113
(58) Field of Search .............................. 422/24, 22, 28, 422/23; 510/113; 424/600, 616

(56) References Cited

U.S. PATENT DOCUMENTS

| 4,394,179 A | 7/1983 | Ellis et al. ..................... 134/7 |
| 4,631,072 A | * 12/1986 | Koller |
| 5,120,499 A | 6/1992 | Baron .......................... 422/24 |
| 5,618,492 A | 4/1997 | Auten et al. ................... 422/22 |
| 5,840,250 A | * 11/1998 | Park et al. ..................... 422/28 |

FOREIGN PATENT DOCUMENTS

| EP | 0 826 633 A | 3/1998 |
| EP | 0 866 101 A | 9/1998 |
| JP | 52-109953 | 9/1977 |
| JP | 62-153217 | 7/1987 |
| JP | 63-59660 | 3/1988 |
| JP | 05-295391 A | * 11/1993 |
| JP | 11-302413 A | * 11/1999 |

* cited by examiner

Primary Examiner—E. Leigh McKane
(74) Attorney, Agent, or Firm—Burr & Brown

(57) ABSTRACT

A method of disinfecting a contact lens is provided, including the steps of preparing a disinfecting liquid which contains water-dispersible fine particles of a titanium oxide dispersed in an aqueous medium, immersing the contact lens in the disinfecting liquid; and irradiating the disinfecting liquid in which the contact lens is immersed, with a light.

18 Claims, No Drawings

METHOD OF DISINFECTING CONTACT LENS AND DISINFECTING LIQUID FOR THE METHOD

This application claims priority from Japanese Patent Application Nos. 11-311487 filed Nov. 1, 1999 and 2000-292664 filed Sep. 26, 2000, the contents of which are incorporated hereinto by reference.

BACKGROUND OF THE INVENTION

1. Field of the Invention

The present invention relates in general to a method of disinfecting a contact lens and a disinfecting liquid used for the method, and more particularly to a technique for disinfecting the contact lens using the disinfecting liquid which is capable of exhibiting an excellent disinfecting effect.

2. Discussion of the Related Art

Conventionally, contact lenses are classified into non-water-contained contact lenses and water-contained contact lenses, or hard contact lenses and soft contact lenses. During a long period of use of the contact lenses, microorganisms such as bacteria and fungi tend to adhere to and proliferate on the surfaces of the contact lenses while the contact lenses are stored after they have been removed from the eyes. Such microorganisms may cause infectious diseases, giving adverse influences on the eyes of the user. In view of the above, the contact lenses need to be disinfected before they are worn on the eyes. In particular, it is indispensable to disinfect the soft contact lenses since the microorganisms are likely to proliferate on the surfaces of the soft contact lenses more often than on the hard contact lenses, increasing a risk of causing the infectious diseases.

For disinfecting the contact lenses, there have been principally practiced a thermal disinfecting method using a suitable boiling and disinfecting device, and a chemical disinfecting method using a suitable chemical agent such as a germicide or a preservative. The thermal disinfecting method undesirably requires a time-consuming boiling operation to disinfect the contact lenses. Accordingly, in recent years, the chemical disinfecting method has been widely employed to disinfect the contact lenses.

In the chemical disinfecting method, the contact lenses are immersed in a disinfecting liquid agent which contains a suitable germicide or preservative, so that the contact lenses are disinfected. As the germicide or preservative contained in the liquid agent, chlorhexidine, benzalconium chloride and thimerosal are disclosed in JP-A-52-109953, JP-A-62-153217 and JP-A-63-59960.

In order to obtain a sufficiently high disinfecting effect, the germicide or preservative as the chemical agent such as chlorhexidine is contained generally in a relatively high concentration in the disinfecting liquid agent. In this case, the germicide or preservative is likely to be adsorbed on the contact lenses on a molecular level, deteriorating wettability at the surfaces of the contact lenses, and causing a change in the properties and configuration of the contact lenses. In some cases, the adsorption of the germicide or preservative on the contact lenses may cause various troubles with the eyes while the contact lenses are worn on the eyes.

To keep the properties and configuration of the contact lenses unchanged, and assure a high degree of safety with the eyes of the lens users, the contact lenses may be disinfected by using a disinfecting liquid agent in which the germicide or preservative is contained in a relatively low concentration. In this case, however, the disinfecting effect to be exhibited by the liquid agent is inevitably lowered, causing contamination of the contact lenses by the microorganisms. Accordingly, when the contact lenses are disinfected by using such a conventional liquid agent, it is necessary to exercise an utmost care in adjusting the concentration of the germicide or preservative included in the liquid agent, making the disinfecting treatment of the contact lenses cumbersome.

The germicide or preservative contained in the contact lens liquid agent used in the chemical disinfecting method acts directly on the microorganisms such as bacteria, thereby exhibiting its disinfecting effect. Accordingly, the germicide or preservative is gradually decomposed and dissipated during use of the liquid agent, so that the liquid agent does not exhibit its disinfecting effect to a satisfactory extent. Thus, it is inevitably impossible to repeatedly use such a contact lens liquid agent, increasing an economical burden on the lens users.

SUMMARY OF THE INVENTION

The present invention was developed in the light of the background art described above. It is a first object of the present invention to provide a novel method of disinfecting a contact lens using a disinfecting liquid which exhibits an excellent disinfecting effect over a long period of time and which is easy and safe to handle.

It is a second object of the invention to provide a contact lens disinfecting liquid which is advantageously used to practice such a disinfecting method.

As one example of a photocatalyst which absorbs a light and exhibits a high degree of oxidation power on its surface, a titanium oxide is generally known. The titanium oxide has been recently attracting an attention since the titanium oxide exhibits a germicidal action with respect to pathogenic microorganisms based on its oxidation power. It is never known to use the titanium oxide having the germicidal action for disinfecting the contact lenses. Up to now, no techniques have been known to effectively disinfect the contact lenses using the titanium oxide.

An extensive study made by the inventors of the present invention under these situations has revealed that the contact lenses can be effectively disinfected by immersing the contact lenses in a suspension which is obtained by dispersing a titanium oxide in the form of fine particles in an aqueous medium, and irradiating the suspension with a light. The present invention was developed based on the above findings.

The above-indicated first object of the present invention may be attained according to a first aspect of the present invention, which provides a method of disinfecting a contact lens comprising the steps of preparing a disinfecting liquid which contains water-dispersible fine particles of a titanium oxide dispersed in an aqueous medium; immersing the contact lens in the disinfecting liquid; and irradiating the disinfecting liquid in which the contact lens is immersed, with a light.

The present method of disinfecting the contact lens utilizes the germicidal action of the titanium oxide based on its photocatalytic action. In the present invention, the water-dispersible fine particles of the titanium oxide are used to provide a disinfecting liquid. Namely, the disinfecting liquid is constituted by a suspension obtained by dispersing the water-dispersible fine particles of the titanium oxide in a suitable aqueous medium, and the contact lens is immersed in the thus prepared disinfecting liquid. With the contact lens being immersed in the disinfecting liquid, the disinfecting liquid is irradiated with a light for disinfecting the contact lens.

In the present method, the fine particles of the titanium oxide are uniformly dispersed in the disinfecting liquid in which the contact lens is immersed, without being aggregated or conglomerated, and these fine particles of the titanium oxide are uniformly irradiated with a light, so that the fine particles of the titanium oxide provide the germicidal or disinfecting action based on the oxidation power exhibited upon exposure to the light. The germicidal or disinfecting action of the fine particles of the titanium oxide which are uniformly dispersed effectively works on the entire surfaces of the contact lens, whereby the contact lens can be sufficiently disinfected. The fine particles of the titanium oxide serving as an effective disinfecting component do not act directly on the microorganisms such as bacteria, but functions as a catalyst. Accordingly, the fine particles of the titanium oxide are not decomposed or dissipated during use of the disinfecting liquid, and exhibit a long-term or permanent disinfecting effect, permitting a repeated use of the disinfecting liquid. Thus, the present arrangement allows an easy and economical disinfecting treatment of the contact lens.

The fine particles of the titanium oxide included in the disinfecting liquid as the effective disinfecting component is not a chemical agent which causes a chemical reaction, and is not likely to be adsorbed on the contact lens upon using the disinfecting liquid, therefore, it is not necessary to take into account adverse influences such as a change of the lens properties or configuration, and various troubles of the eyes of the lens users, which adverse influences are experienced when a contact lens liquid agent including a conventional germicide or preservative is used to disinfect the contact lens. Accordingly, the present arrangement assures safe and easy handling of the disinfecting liquid, and a simple disinfecting treatment of the contact lens.

In a preferred form of the above first aspect of the present invention, the fine particles of the titanium oxide have an average particle size of not larger than 15 nm. Preferably, the fine particles of the titanium oxide are contained in the disinfecting liquid in a concentration of 1100 ppm. These arrangements permit the disinfecting liquid to have a sufficiently high degree of transparency, so that the light is effectively incident on the fine particles of the titanium oxide, for thereby enhancing the disinfecting effect with respect to the contact lens. Like the conventional contact lens liquid agent, the present disinfecting liquid permits a visual observation of the contact lens immersed therein.

In another preferred form of the above first aspect of the present invention, the disinfecting liquid further contains sodium chloride. The inclusion of sodium chloride assures an enhanced disinfecting effect of the disinfecting liquid with respect to the contact lens. In the present disinfecting method, it is preferable to apply ultrasonic waves to the disinfecting liquid or oscillate the disinfecting liquid, prior to or upon incidence of the light thereon, so that the fine particles of the titanium oxide can be uniformly dispersed in the disinfecting liquid to assure a further improved disinfecting effect.

When the disinfecting liquid includes the sodium chloride, the concentration of the sodium chloride is preferably held in a range of 0.7~1.2 wt. %. Even if the disinfecting liquid may enter the eye of the lens user when the contact lens which has been disinfected according to the present disinfecting method is worn on the eye with the disinfecting liquid adhering to the surfaces of the contact lens, the disinfecting liquid containing the sodium chloride whose concentration is kept within the above range is effective to reduce eye irritation.

In a further preferred form of the above first aspect of the present invention, the disinfecting liquid further contains, as needed, at least one of a chelating agent, a buffer, a surface active agent, a thickener, a preservative, a germicide, and an oxidizing agent, so that the disinfecting liquid has an intended property given by the at least one additive.

The oxidizing agent is preferably selected from among a hydrogen peroxide, ozone water, a sodium peroxide, a magnesium peroxide, and a silver oxide, for instance. It is particularly preferable to use the hydrogen peroxide to promote the photocatalytic action of the fine particles of the titanium oxide. For preventing the peroxide remaining in the disinfecting liquid from adversely influencing the eye of the lens user, the hydrogen peroxide is contained in the disinfecting liquid preferably in a concentration of 10~300 ppm.

Preferably, the disinfecting liquid further contains at least one metal ion, together with the hydrogen peroxide.

In a still further preferred form of the above first aspect of the present invention, the light is selected from the group consisting of a natural light, an ultraviolet light, a visible light, a light emitted from an incandescent lamp, and a light emitted from a fluorescent lamp.

In a yet further preferred form of the above first aspect of the present invention, the disinfecting liquid is irradiated with the light having a wavelength of 320~410 nm.

In another preferred form of the above first aspect of the invention, the light has an intensity in a range of 0.1~50 mW/cm$^2$ at a wavelength of about 365 nm.

The above-indicated second object of the present invention may be attained according to a second aspect of the invention, which provides a contact lens disinfecting liquid which exhibits a disinfecting effect with respect to a contact lens by being irradiated with a light, the contact lens disinfecting liquid being characterized by containing water-dispersible fine particles of a titanium oxide which are dispersed in an aqueous medium.

A contact lens is immersed in the present contact lens disinfecting liquid wherein the titanium oxide is dispersed in a suitable aqueous medium in the form of fine particles, and the disinfecting liquid is irradiated with a light, so that the fine particles of the titanium oxide exhibit an excellent disinfecting or germicidal action based on the photocatalytic action thereof. Further, the disinfecting action of the titanium oxide lasts for a long period of time. Moreover, the present disinfecting liquid is safe and simple to handle.

In a preferred form of the above second aspect of the present invention, the fine particles of the titanium oxide have an average particle size of not larger than 15 nm. Preferably, the fine particles of the titanium oxide are contained in the disinfecting liquid in a concentration of 1~100 ppm. As in the above-described first aspect of the present invention, it is preferable that the contact lens disinfecting liquid according to the second aspect of the invention further contains sodium chloride.

As needed, the present contact lens disinfecting liquid may further contain an oxidizing agent such as a hydrogen peroxide.

In a preferred form of the above second aspect of the present invention, the contact lens disinfecting liquid further contains at least one metal ion, together with the oxidizing agent.

DETAILED DESCRIPTION OF THE INVENTION

The present method of disinfecting a contact lens is characterized by preparing a disinfecting liquid which is a suspension obtained by dispersing water-dispersible fine particles of a titanium oxide in an aqueous medium such as purified water, immersing a contact lens to be disinfected in the disinfecting liquid, and irradiating the disinfecting liquid in which the contact lens is immersed, with a light, so that the contact lens is disinfected.

The contact lens disinfecting liquid according to the present invention contains the titanium oxide generally known as a photocatalyst. Described in detail, the titanium oxide in the form of fine particles are uniformly dispersed in a suitable aqueous medium without being aggregated or conglomerated. With the contact lens being immersed in the disinfecting liquid, the disinfecting liquid is irradiated with a light. In this case, the light is uniformly incident on the fine particles of the titanium oxide which are uniformly dispersed in the disinfecting liquid so as to be uniformly present around the contact lens immersed in the disinfecting liquid. Each fine particle of the titanium oxide receives and absorbs the light incident thereon, so as to exhibit a high degree of oxidation power on its surface based on the photocatalytic action. Accordingly, the contact lens can be sufficiently disinfected over the entire surfaces owing to an effective germicidal action of the titanium oxide based on the oxidation power described above.

The disinfecting effect attained according to the present invention is owing to the photocatalytic action of the fine particles of the titanium oxide contained in the disinfecting liquid. In this respect, the fine particles of the titanium oxide are not decomposed or dissipated during use of the disinfecting liquid, so that the disinfecting liquid exhibits a long-term or lasting disinfecting effect. This arrangement permits a repeated use of the disinfecting liquid, for thereby minimizing an economical burden on the user.

Unlike the chemical agent in the form of the germicide or preservative which is used in the conventional chemical disinfecting method and which causes a certain chemical reaction, the fine particles of the titanium oxide used as the effective disinfecting component in the present disinfecting liquid are not likely to be adsorbed on the contact lens. Accordingly, even after the contact lens has been disinfected with the disinfecting liquid containing such fine particles of the titanium oxide, the fine particles are not adsorbed on the contact lens, preventing a change of the properties and configuration of the contact lens and avoiding eye troubles. Therefore, in the disinfecting treatment according to the present invention, it is not required to pay so much attentions in handling the disinfecting liquid, assuring safe and easy handling of the disinfecting liquid and simplifying the disinfecting procedure of the contact lens.

While the particle size of the fine particles of the titanium oxide is determined so as to permit the fine particles to be dispersed in a suitable aqueous medium, it is preferable that the fine particles of the titanium oxide have an average particle size of not larger than 15 nm, preferably not larger than 10 nm. If the particle size of the titanium oxide is excessively large, the disinfecting liquid does not have a sufficiently high degree of transparency. In this case, when a light which is emitted from a suitable light source is incident on the disinfecting liquid, the light is prevented from transmitting through the disinfecting liquid by the fine particles, existing in a portion of the disinfecting liquid on the side relatively near the light source. Therefore, the fine particles of the titanium oxide existing in the other portion of the disinfecting liquid on the side remote from the light source are prevented from being irradiated with the light, causing a considerable deterioration of the disinfecting effect of the disinfecting liquid. In addition, it would be difficult to visually observe the presence of the contact lens immersed in the disinfecting liquid if the transparency of the disinfecting liquid was low due to excessively large particle size of the fine particles of the titanium oxide.

The fine particles of the titanium oxide having the particle size described above are contained in the disinfecting liquid in a concentration which assures the intended effect. In general, the fine particles of the titanium oxide are contained in the disinfecting liquid generally in a concentration of 1~100 ppm, preferably 1~50 ppm, for the entire volume of the disinfecting liquid. If the concentration of the fine particles of the titanium oxide is excessively low, the disinfecting effect of the disinfecting liquid is insufficient. On the contrary, if the concentration of the fine particles of the titanium oxide is excessively high, the transparency of the disinfecting liquid is reduced, preventing the fine particles of the titanium oxide from being efficiently exposed to the incident light and accordingly deteriorating the disinfecting effect of the disinfecting liquid. Further, the excessively high concentration of the fine particles of the titanium oxide makes it difficult to visually observe the presence of the contact lens immersed in the disinfecting liquid.

The present contact lens disinfecting liquid wherein the fine particles of the titanium oxide are dispersed in an appropriate concentration in the aqueous medium may preferably contain a predetermined amount of sodium chloride. The combined use of the fine particles of the titanium oxide and the predetermined amount of the sodium chloride enhances the disinfecting effect of the disinfecting liquid with respect to the contact lens although the mechanism of the synergistic effect is not clear. The amount of the sodium chloride is desirably determined such that the eye of the lens user does not suffer from any irritation even if the disinfecting liquid may enter the eye of the lens user when the disinfected contact lens is worn on the eye with the disinfecting liquid adhering to the surfaces of the contact lens. In view of this, the sodium chloride is contained in the disinfecting liquid generally in a concentration of 0.7~1.2 wt. %, preferably 0.8~1.1 wt. %.

The present contact lens disinfecting liquid may further contain, as needed, various known additives as used in the conventional contact lens liquid agent. For instance, the disinfecting liquid may contain at least one of a chelating agent, a buffer, a surface active agent, a thickener, a preservative, a germicide, and an oxidizing agent. The additives to be contained in the disinfecting liquid should be safe to the living body and should not give an adverse influence on the effects provided by the fine particles of the titanium oxide. The additives are contained in the disinfecting liquid in amounts that do not inhibit the effects provided by the fine particles of the titanium oxide.

When the oxidizing agent is included as an additive in the disinfecting liquid, at least one of a hydrogen peroxide, ozone water, a sodium peroxide, a magnesium peroxide, and a silver oxide is used as the oxidizing agent, for instance.

Among the oxidizing agents described above, the hydrogen peroxide and the ozone water themselves exhibit a sufficiently high germicidal or antimicrobial effect, and are preferably used as the oxidizing agent in the disinfecting liquid of the present invention. The hydrogen peroxide and the ozone water exhibit a high degree of germicidal effect because the hydrogen peroxide itself is an active oxygen having a high degree of oxidation power while the ozone contained in the ozone water is an active oxygen having the second highest oxidation power in the natural world, next to fluorine.

When the present contact lens disinfecting liquid contains the oxidizing agent (peroxide) in addition to the fine particles of the titanium oxide, the disinfecting liquid is capable of exhibiting a significantly high degree of germicidal or antimicrobial effect owing to the disinfecting effect based on the photocatalytic action of the fine particles of the titanium oxide and the germicidal or antimicrobial effect of the oxidizing agent (peroxide), than a disinfecting liquid containing only one of the fine particles of the titanium oxide and the oxidizing agent (peroxide). Described in detail, the oxidizing agent (peroxide) promotes the photocatalytic action of the fine particles of the titanium oxide to activate formation of the active oxygen, resulting in an efficient decomposition reaction of an organic substance such as endotoxin (J. Antibact. Antifung. Agents Vol. 26, No. 11, pp.611~620, 1998).

Since the combined use of the fine particles of the titanium oxide and the oxidizing agent (peroxide) assures the synergistically enhanced germicidal and antimicrobial effect, the concentration of the oxidizing agent can be reduced to $\frac{1}{100}$ or lower of the concentration required when the disinfecting liquid contains only the oxidizing agent (peroxide). For instance, the concentration of the oxidizing agent can be made as low as 10~300 ppm or 10~50 ppm.

When the oxidizing agent (peroxide) is contained in the disinfecting liquid in a considerably lower concentration as described above, it is not necessary to effect a conventionally required neutralization treatment to neutralize the oxidizing agent (peroxide) for assuring economical and easy handling of the disinfecting liquid. Since the concentration of the oxidizing agent (peroxide) can be lowered as described above, the eye of the lens user is less likely to suffer from irritation even when the disinfected contact lens is worn on the eye with the disinfecting in liquid remaining on its surfaces.

When the disinfecting liquid contains the oxidizing agent (peroxide) described above, it is possible to add at least one metal ion to the disinfecting liquid. The addition of the metal ion is effective to promote the photocatalytic action of the fine particles of the titanium oxide, for thereby activating the formation of the active oxygen. As the metal ion, an iron ion, a silver ion, or an aluminum ion is used, for instance. At least one of those ions is preferably contained in the disinfecting liquid. Among those metal ions, a divalent iron ion has a particularly high effect of promoting the photocatalytic action of the fine particles of the titanium oxide, so that the divalent metal iron ion contributes to an improvement of the germicidal or antimicrobial efficacy of the disinfecting liquid.

The chelating agent to be included as the additive in the present contact lens disinfecting liquid is effective to prevent the metal ion such as a calcium ion from depositing on the surfaces of the contact lens. Examples of the chelating agent include ethylenediamine tetraacetic acid, citric acid, gluconic acid, tartaric acid, phytic acid and salts thereof (e.g. sodium salt). The buffer to be included as the additive in the present disinfecting liquid adjusts the pH of the disinfecting liquid to an appropriate level for the purpose of maintaining the physical properties and configuration of the contact lens. Typical examples of the buffer are citric acid, malic acid, lactic acid, ascorbic acid, maleic acid, gluconic acid, phosphoric acid, boric acid, amino acid such as glycine or glutamic acid, tris(hydroxymethyl)aminomethane, and salts thereof (e.g., sodium salt).

The surface active agent or surfactant to be included as an additive in the present disinfecting liquid is suitably selected from among known anionic, nonionic, amphoteric, and cationic surface active agents. Owing to the surface active agent included in the disinfecting liquid, the disinfecting liquid is capable of exhibiting a cleaning effect with respect to lipid stains. As the thickener used to adjust the viscosity of the disinfecting liquid, a suitable viscous base is employed such as polyvinyl alcohol, poly-N-vinylpyrolidone, polyethylene glycol, polyacrylamide, a hydrolyzed product of polyacrylamide, polyacrylic acid, hydroxyethyl cellulose, carboxymethyl cellulose, methylhydroxyethyl cellulose, methylhydroxypropyl cellulose, methyl cellulose, gelatin, sodium alginate, sodium chondroitin sulfate, xanthan gum, gum arabic, or guar gum. The disinfecting liquid according to the present invention may contain, as the preservative or germicide, other known compounds which exhibit preservative or germicidal efficacy.

As the aqueous medium used in the present invention, there may be employed a solution which is principally constituted by water such as a saline solution, an aqueous solution containing sodium chloride, and a known contact lens storing or cleaning liquid, in addition to tap water, purified water, and distilled water.

In a method of disinfecting a contact lens according go to the present invention, a contact lens to be disinfected is immersed in the disinfecting liquid prepared as described above, and the disinfecting liquid is irradiated with a light, so that the contact lens immersed in the disinfecting liquid is disinfected. In this disinfecting treatment, the contact lens disinfecting liquid of the present invention is accommodated in a suitable container which at least partially permits light transmission and the contact lens to be disinfected is immersed in the disinfecting liquid accommodated in the container. Then, the container is irradiated with a light, so that the light is incident on the disinfecting liquid (the fine particles of the titanium oxide) in the container, whereby the contact lens is disinfected. In the present method, the container is preferably formed of a transparent material, and is irradiated with a light in a plurality of directions for increased irradiation efficiency. Further, it is preferable to apply ultrasonic waves to the disinfecting liquid, or oscillate the disinfecting liquid by oscillating the container in which the disinfecting liquid is accommodated, for instance, prior to or upon incidence of the light. According to this arrangement, the fine particles of the titanium oxide in the disinfecting liquid can be uniformly dispersed, resulting in an enhanced disinfecting effect of the disinfecting liquid.

The light which is incident on the disinfecting liquid in which the contact lens is immersed is not particularly limited, as long as the light has a wavelength of about 320~410 nm. For instance, a natural light, an ultraviolet or visible light emitted from a suitable light emitting device or light source, and a light emitted from an incandescent lamp or a fluorescent lamp can be employed. In the present invention, it is preferable to use a light having an intensity generally in a range of 0.1~50 mW/cm$^2$, preferably 0.5~30 mW/cm$^2$ at a wavelength of about 365 nm. If the light intensity is excessively low, the photocatalytic action of the fine particles of the titanium oxide is reduced, resulting in an insufficient disinfecting effect. On the contrary, the excessively high light intensity will generate heat, causing deterioration of the contact lens such as a change of its color to yellow.

The period of time during which the contact lens is disinfected by the disinfecting liquid while it is exposed to a light is suitably determined depending on a desired degree of disinfection of the contact lens, and various factors such as the kind of the contact lens to be disinfected, and the wavelength and intensity of the light to be incident on the disinfecting liquid. For sufficiently obtaining the desired disinfecting effect, the disinfecting liquid generally needs to be irradiated with the light for at least 15 minutes. For efficient disinfecting treatment, the disinfecting liquid is irradiated with the light for up to about twelve hours, preferably up to about six hours.

According to the procedure described above, the contact lens can be simply and effectively disinfected in an economical manner while assuring easy handling of the disinfecting liquid.

After the disinfecting treatment according to the present invention, the contact lens is taken out of the disinfecting liquid and is directly worn on the eye of the lens user. Alternatively, the contact lens may be rinsed with a saline solution, for instance, before the contact lens is worn on the eye.

The present method of disinfecting the contact lens and the present disinfecting liquid used in the method can be applied to any known kinds of contact lenses such as low-water-content and high-water-content soft contact lenses, and hard contact lenses, irrespective of the materials of those contact lenses.

While the contact lens disinfecting liquid of the present invention is used to disinfect the contact lens before it is worn on the eye of the lens user, the disinfecting liquid, which exhibits its disinfecting effect by irradiation with the light, can be used as a contact lens storing liquid. For instance, during transportation of contact lens products, the contact lens products are accommodated in a suitable transportation container, together with the disinfecting liquid, which container permits light transmission. In this case, the contact lens products in the container are stored in a disinfected state with the disinfecting liquid being irradiated with natural light during the transportation of the contact lens products.

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

<Preparation of Disinfecting Liquid Specimens>

There were prepared various disinfecting liquid specimens Nos. 16 in the following manner. A commercially available titanium oxide suspension ("Mano Tek" available from C.I. KASEI CO., LTD., Japan) in which fine particles of a titanium oxide ($TiO_2$) having an average particle size of 5 nm are contained in a concentration of 15 wt. %, was diluted with a sterile saline solution (NaCl aqueous solution) which contains sodium chloride (NaCl) in a concentration of 0.9 wt. %. The thus prepared disinfecting liquid specimens Nos. 1~6 contain the fine particles of the titanium oxide in respective concentrations indicated in the following Tables 1 and 2.

A disinfecting liquid specimen No. 7 was prepared by diluting the titanium oxide suspension as used in preparing the specimens Nos. 1~6 with a sterile purified water, so that the disinfecting liquid specimen No. 7 contains the fine particles of titanium oxide in a concentration indicated in the Table 2.

The sterile saline solution containing sodium chloride in a concentration of 0.9 wt. % as was used in the specimen No. 1 was prepared as a disinfecting liquid specimen No. 8 which does not contain the titanium oxide suspension.

Disinfecting liquid specimens Nos. 9~13 were prepared by diluting the titanium oxide suspension as was used in the specimens Nos. 1~6 with the sterile saline solution containing sodium chloride in a concentration of 0.9 wt. %, and adding thereto hydrogen peroxide in respective amounts as indicated in the following Table 3.

Further, there was prepared a disinfecting liquid specimen No. 14 which contained hydrogen peroxide in an amount indicated in the Table 3 containing neither the sterile saline solution nor the titanium oxide suspension.

<Test for Examining the Disinfecting Effect>

Each of the thus prepared disinfecting liquid specimens Nos. 1~14 was examined of its disinfecting (germicidal) effect in the following manner. Initially, a suitable amount of each disinfecting liquid specimen was put into a sterile transparent test tube. Then, S.a. (*Serratia marcescens:ATCC 13880*) as test bacterium was inoculated at about $10^6$ cfu/mL. The test tubes in which the disinfecting liquid specimens Nos. 1, 3, 5, 7, 8, 9, 11, 13 and 14 were accommodated, respectively, were irradiated with a UV light having a wavelength of about 365 nm, which was emitted from a UV lamp and whose intensity was 3.3 $mW/cm^2$. The test tubes were irradiated with the UV light for respective time periods indicated in the Tables 1~3.

Viable cell counts were measured for the disinfecting liquid specimens Nos. 1, 3, 5, 7, 8, 9, 11, 13 and 14 which had been irradiated with the UV light, and the disinfecting liquid specimens Nos. 2, 4, 6, 10 and 12 which had not been irradiated with the UV light, in the following manner. A predetermined amount of each specimen was taken out of the corresponding test tube, and was diluted with a sterile saline solution, so as to provide a diluted sample. A viable cell count for 1 mL of the thus obtained diluted sample was measured according to a plate method. For the disinfecting liquid Em specimens which had not been irradiated with the UV light, the viable cell counts were measured after the specimens had been kept at room temperature for respective time periods indicated in the Tables 13. On the basis of the measured viable cell counts, there were calculated a viable cell count per 1 mL of each diluted sample after exposure to the UV light and a viable cell count per 1 mL of each diluted sample after it was kept at room temperature for a predetermined time. Then, an amount of reduction of the bacteria was calculated in logarithm (log reduction) according to the following equation. The results of calculation are indicated in Tables 1~3.

Reduction amount [in logarithm]=log (viable cell count per 1 mL of each specimen immediately after inoculation)–log (viable cell count per 1 mL of each specimen after irradiation with UV light or exposure to room temperature for a predetermined time)

TABLE 1

| disinfecting liquid specimen No. | 1 | 2 | 3 | 4 |
|---|---|---|---|---|
| $TiO_2$ (ppm)* | 3 | 3 | 15 | 15 |

TABLE 1-continued

| UV-irradiated or not | UV-irradiated for 3 hours | kept at room temperature for 3 hours | UV-irradiated for 3 hours | kept at room temperature for 3 hours |
|---|---|---|---|---|
| log reduction | 1.3 | −0.06 | 1.8 | 0.05 |

*concentration the disinfecting liquid specimen

TABLE 2

| disinfecting liquid specimen No. | 5 | 6 | 7 | 8 |
|---|---|---|---|---|
| $TiO_2$ (ppm)* | 15 | 15 | 15 | — |
| UV-irradiated or not | UV-irradiated for 6 hours | kept at room temperature for 6 hours | UV-irradiated for 3 hours | UV-irradiated for 6 hours |
| log reduction | 2.3 | −0.23 | 0.66 | −0.03 |

*concentration in the disinfecting liquid specimen

TABLE 3

| disinfecting liquid specimen No. | 9 | 10 | 11 | 12 | 13 | 14 |
|---|---|---|---|---|---|---|
| $TiO_2$ (ppm)* | 15 | 15 | 15 | 15 | 15 | — |
| $H_2O_2$ (ppm)* | 30 | 30 | 10 | 10 | 300 | 30 |
| UV-irradiated or not | UV-irradiated for 3 hours | kept at room temp. for 3 hours | UV-irradiated for 3 hours | kept at room temp. for 3 hours | UV-irradiated for 3 hours | UV-irradiated for 3 hours |
| log reduction | 3.8 | 0.38 | 2.4 | −0.06 | 3.9 | 0.03 |

*concentration in the disinfecting liquid specimen

As is apparent from the results of Tables 1~3, in each of the disinfecting liquid specimens Nos. 1, 3, 5, 7, 9, 11 and 13 of the present invention which had been irradiated with the UV light, the log reduction value indicative of the amount of reduction of bacteria was relatively large, so that the disinfecting liquid specimens according to the present invention exhibited a high degree of germicidal efficacy. Namely, it is recognized that the disinfecting liquid specimens prepared according to the present invention is capable of assuring an enhanced disinfecting effect. In particular, the log reduction values were larger than 1, in other words, more than 90% of the viable cells were eliminated or killed, in the disinfecting liquid specimens Nos. 1, 3 and 5 which contained sodium chloride. The results indicate that the combined use of the fine particles of titanium oxide and the sodium chloride is effective to considerably improve the disinfecting effect of the disinfecting liquid. Further, the comparisons of the log reduction values of the disinfecting liquid specimens No. 1 and No. 3, and of the disinfecting liquid specimens No. 3 and No 5 revealed that the disinfecting effect can be advantageously improved by increasing the concentration of the fine particles of titanium oxide within a suitable range or appropriately increasing the UV irradiation time.

The log reduction values were larger than 2 in the disinfecting liquid specimens Nos. 9, 11 and 13 which contained the hydrogen peroxide in addition to the sodium chloride. Accordingly, it is recognized that the disinfecting effect of the disinfecting liquid can be enhanced when the disinfecting liquid contains the hydrogen peroxide in addition to the fine particles of the titanium oxide and the sodium chloride.

In contrast, the disinfecting liquid specimens Nos. 2, 4, 6, 10 and 12 exhibited lower disinfecting effects than the specimens Nos. 1, 3, 5, 9 and 11 of the present invention. This is because the specimens Nos. 2, 4, 6, 10 and 12 were not irradiated with the UV light although those specimens were prepared according to the present invention. The disinfecting liquid specimen No. 8 which does not contain the fine particles of the titanium oxide did not exhibit a disinfecting effect. The disinfecting liquid specimen No. 14 which contains the hydrogen peroxide and which does not contain the fine particles of the titanium oxide exhibited substantially no disinfecting effect.

What is claimed is:

1. A method of disinfecting a contact lens comprising the steps of:
    preparing a disinfecting liquid which contains water-dispersible fine particles of a titanium oxide dispersed in an aqueous medium;
    immersing said contact lens in said disinfecting liquid; and
    irradiating said disinfecting liquid in which said contact lens is immersed, with a light.

2. A method according to claim 1, wherein said fine particles of the titanium oxide have an average particle size of not larger than 15 nm.

3. A method according to claim 1, wherein said fine particles of the titanium oxide are present in said disinfecting liquid in a concentration of 1~100 ppm.

4. A method according to claim 1, wherein said disinfecting liquid further contains sodium chloride.

5. A method according to claim 4, wherein said sodium chloride is present in said disinfecting liquid in a concentration range of 0.7~1.2 wt. %.

6. A method according to claim 1, wherein said disinfecting liquid further contains at least one of a chelating agent, a buffer, a surface active agent, a thickener, a preservative, a germicide and an oxidizing agent.

7. A method according to claim 6, wherein said oxidizing agent is a hydrogen peroxide.

8. A method according to claim 7, wherein said hydrogen peroxide is present in said disinfecting liquid in a concentration range of 10~300 ppm.

9. A method according to claim 6, wherein said disinfecting liquid further contains at least one metal ion, together with said oxidizing agent.

10. A method according to claim 1, wherein said light is selected from the group consisting of a natural light, an ultraviolet light, a visible light, a light emitted from an incandescent lamp, and a light emitted from a fluorescent lamp.

11. A method according to claim 1, wherein said disinfecting liquid is irradiated with said light having a wavelength of 320~410 nm.

12. A method according to claim 11, wherein said light has an intensity in a range of 0.1~50 mW/cm$^2$ at a wavelength of about 365 nm.

13. A contact lens disinfecting liquid which exhibits a disinfecting effect with respect to a contact lens by being irradiated with a light, wherein the improvement comprises:

said contact lens disinfecting liquid containing water-dispersible fine particles of a titanium oxide which arc dispersed in an aqueous medium, and wherein said fine particles of said titanium oxide have an average article size of not larger than 15 mm, and wherein said fine particles of said titanium oxide are present in said contact lens disinfecting liquid in a concentration of 1~100 ppm.

14. A contact lens disinfecting liquid according to claim 13, further containing sodium chloride.

15. A contact lens disinfecting liquid according to claim 13, further containing an oxidizing agent.

16. A contact lens disinfecting liquid according to claim 15, wherein said oxidizing agent is a hydrogen peroxide.

17. A contact lens disinfecting liquid according to claim 15, further containing at least one metal ion.

18. A contact lens disinfecting liquid according to claim 16, wherein said oxidizing agent is present in a concentration range of 10 ppm to 300 ppm.

* * * * *

UNITED STATES PATENT AND TRADEMARK OFFICE
CERTIFICATE OF CORRECTION

PATENT NO.    : 6,790,409 B1
DATED         : September 14, 2004
INVENTOR(S)   : Chikako Nakamura et al.

It is certified that error appears in the above-identified patent and that said Letters Patent is hereby corrected as shown below:

Title page,
Item [54], Title, "OF" should read -- FOR --
Item [56], References Cited, FOREIGN PATENT DOCUMENTS, change "63-59660" to -- 63-59960 --
Item [57], ABSTRACT,
Line 5, delete ";" after "liquid"
Line 6, delete "," after "immersed"

Column 14,
Line 2, change "arc" to -- are --
Line 4, change "article" to -- particle --
Line 5, change "mm" to -- nm --

Signed and Sealed this

Twenty-sixth Day of July, 2005

JON W. DUDAS
*Director of the United States Patent and Trademark Office*